(12) United States Patent
Kolb et al.

(10) Patent No.: US 11,097,319 B2
(45) Date of Patent: Aug. 24, 2021

(54) METHOD AND CONTAINER FOR CLEANING THE MEMBRANE OF A NEBULIZER

(71) Applicant: Vectura Delivery Devices Limited, Wiltshire (GB)

(72) Inventors: Tobias Kolb, Gauting (DE); Bernhard Muellinger, Gauting (DE); Jana Strixner, Gauting (DE); Ulf Krueger, Gauting (DE)

(73) Assignee: VECTURA DELIVERY DEVICES LIMITED, Wiltshire (GB)

( * ) Notice: Subject to any disclaimer, the term of this patent is extended or adjusted under 35 U.S.C. 154(b) by 74 days.

(21) Appl. No.: 16/496,250

(22) PCT Filed: Mar. 19, 2018

(86) PCT No.: PCT/EP2018/056909
§ 371 (c)(1),
(2) Date: Sep. 20, 2019

(87) PCT Pub. No.: WO2018/172292
PCT Pub. Date: Sep. 27, 2018

(65) Prior Publication Data
US 2020/0023412 A1 Jan. 23, 2020

(30) Foreign Application Priority Data

Mar. 20, 2017 (EP) .................................. 17161909
Mar. 20, 2017 (EP) .................................. 17161911

(51) Int. Cl.
*B08B 3/08* (2006.01)
*A61M 11/04* (2006.01)

(52) U.S. Cl.
CPC ............... *B08B 3/08* (2013.01); *A61M 11/04* (2013.01); *A61M 2205/0211* (2013.01);
(Continued)

(58) Field of Classification Search
CPC .... A61M 11/00; A61M 11/005; A61M 15/00; A61M 15/001; A61M 15/0028;
(Continued)

(56) References Cited

U.S. PATENT DOCUMENTS

2002/0011247 A1 1/2002 Ivri et al.
2008/0006264 A1* 1/2008 Gallem ............. A61M 15/0021
128/200.14
(Continued)

FOREIGN PATENT DOCUMENTS

EP 2724741 4/2014
JP 2004283244 A 10/2004
(Continued)

OTHER PUBLICATIONS

English language translation of Office Action dated Oct. 28, 2020, Japanese Patent Application No. 2019-551511.
(Continued)

*Primary Examiner* — Joseph D. Boecker
(74) *Attorney, Agent, or Firm* — Barnes & Thornburg LLP; Ryan P. Cox (57) ABSTRACT

The present invention provides a single-use, pre-packaged, sealed container (1) for use with a nebulizer device having an aerosol generator comprising a membrane, the container containing a cleaning liquid (3) and being configured to fit onto the nebulizer device, so that the container is held in place on the nebulizer device and the membrane is immersed in the liquid. The invention also provides a strip comprising a plurality of containers (10), wherein each container is detachable from the rest of the strip; a pack comprising a
(Continued)

multi-day supply of a drug and containers; and a method for cleaning the membrane of a nebulizer device using the container.

11 Claims, 9 Drawing Sheets

(52) U.S. Cl.
CPC . *A61M 2205/0294* (2013.01); *A61M 2209/06* (2013.01); *A61M 2209/10* (2013.01)

(58) Field of Classification Search
CPC .......... A61M 15/0043; A61M 15/0051; A61M 15/0085; A61M 2209/10; B05B 15/55; B08B 3/08
See application file for complete search history.

(56) References Cited

U.S. PATENT DOCUMENTS

| | | | |
|---|---|---|---|
| 2009/0200182 A1* | 8/2009 | Post-Smith | B65D 43/162 206/5.1 |
| 2011/0041875 A1 | 2/2011 | Araki | |
| 2014/0034052 A1 | 2/2014 | Glusker et al. | |
| 2015/0165137 A1 | 6/2015 | Mullinger et al. | |
| 2015/0352297 A1 | 12/2015 | Stedman et al. | |
| 2016/0354557 A1 | 12/2016 | Allnutt et al. | |
| 2017/0232211 A1* | 8/2017 | Gallem | A61M 15/0065 128/203.12 |
| 2019/0192791 A1* | 6/2019 | Osoegawa | A61M 15/0085 |

FOREIGN PATENT DOCUMENTS

| | | |
|---|---|---|
| RU | 2141351 C1 | 11/1999 |
| WO | 9963946 A2 | 12/1999 |
| WO | 2007088364 | 8/2007 |
| WO | 2010002039 A1 | 1/2010 |
| WO | 2011058477 A1 | 5/2011 |
| WO | 2011083744 A1 | 7/2011 |
| WO | 2012112815 A2 | 8/2012 |
| WO | 2013082180 A1 | 6/2013 |
| WO | 2014072808 | 5/2014 |
| WO | 2015128375 A1 | 9/2015 |
| WO | WO-2016026802 A1 * | 2/2016 ........ A61M 15/0005 |

OTHER PUBLICATIONS

English language translation of Office Action dated Nov. 20, 2020, Japanese Patent Application No. 2019-551661.
English language translation of Office Action dated Feb. 9, 2021, Chinese Patent Application No. 201880019057.2.
Written Opinion of the International Preliminary Examining Authority in PCT Application No. PCT/EP2018/056909 dated Feb. 11, 2019.
Notification of Transmittal of the International Preliminary Report on Patentability in PCT Application No. PCT/EP2018/056909 dated Jun. 13, 2019.

* cited by examiner

METHOD AND CONTAINER FOR CLEANING THE MEMBRANE OF A NEBULIZER

CROSS-REFERENCE TO RELATED APPLICATIONS

This application is a United States national stage of International Application No. PCT/EP2018/056909, filed Mar. 19, 2018, which was published as International Publication No. WO 2018/172292, and which claims benefit of European Application No. 17161909.1, filed Mar. 20, 2017 and European Application No. 17161911.7, filed Mar. 20, 2017, the entire contents of which are each hereby expressly incorporated herein by reference.

TECHNICAL FIELD OF THE INVENTION

The present invention relates to nebulizers which have a membrane, mesh or nozzle plate containing pores. In particular, the invention relates to a method and a container for cleaning and maintaining the membrane.

BACKGROUND TO THE INVENTION

Aerosolized liquids are used in many applications, such as delivery of bioactive agents, e.g. in medical inhalation therapies, insecticide delivery and disinfection; diffusion of cosmetic products such as perfumes or odour generation; humidification of air or substrates like paper or textiles; fuel combustion; and inkjet printing.

Aerosols for medical inhalation therapy generally comprise an active ingredient for the prevention, management, treatment or alleviation of a disease, condition or symptom. The active, often also referred to as drug, drug substance, active compound, pharmaceutical, active pharmaceutical ingredient (API), or bioactive agent, is dissolved, dispersed or suspended in a liquid carrier (usually aqueous) to form an aerosolisable (nebulisable) drug formulation.

In recent years, the pharmaceutical industry has become increasingly interested in drug delivery devices which transport aerosols deeper into the lungs; ideally reaching even the smallest branches of the peripheral lungs, such as bronchioles and alveoli. Such devices allow administration of systemically active drugs by the respiratory route, rather than just administering locally active drugs. Improved deep lung deposition results in an optimised systemic effect and hence potential dose reductions. This requires a homogeneous distribution of aerosol droplets with a droplet size of around 5 µm. In order to achieve this, the liquid formulation is typically aerosolised by a nebulizer, such as a vibrating mesh nebulizer or a spray-nozzle nebulizer.

Vibrating mesh nebulizers typically comprise a vibrator, such as piezoelectric element which is excited at ultrasonic frequencies in order to induce vibration; a membrane (sometimes called a mesh), and a reservoir, which supplies the liquid drug formulation to the membrane. The membrane is either permanently fixed to the vibrator (e.g. by gluing, brazing, crimping or welding) or detachably arranged in contact with the vibrator (e.g. by a spring-coil or the like) to allow vibrations of the piezoelectric element to be transmitted to the membrane. The membrane has a large number of micro-pores (i.e. through holes) which typically have a diameter of 1 µm to 200 µm. For medical inhalation, the pores have a diameter below 20 µm, e.g. 3 µm to obtain droplets of about 5 µm in size. Nozzle-spray nebulizers are another type of inhalation device which use a membrane with small pores. These form the aerosol by forcing liquid under pressure through holes in a nozzle plate.

During use, the pores of the membrane can become clogged with residue from the liquid which is aerosolized. This can lead to a reduction in performance, in particular a reduction of the rate of aerosol generation. Moreover, for some indications such as cystic fibrosis, disinfection is also required because of the serious worsening of the patient's health that could result from infection. The membrane therefore requires regular cleaning or replacement.

Some cleaning methods require the membrane to be removed from the nebulizer and immersed in a cleaning liquid. However, this suffers from the drawback that some patients do not always use appropriate cleaning liquids, or do not take sufficient care to carry out cleaning in a hygienic manner, or do not clean for sufficiently long. Therefore specific cleaning devices have been developed.

WO 2010/002039 and US 2011/0041875 disclose a cleaning device in which cleaning liquid is supplied to the membrane, and then collected after cleaning by means of valves and a pump.

US 2008/0006264 and EP 1875936 disclose a device and method for cleaning a nebulizer membrane. The cleaning device comprises means for supplying cleaning liquid to the aerosol side of the membrane (i.e. the opposite side of the membrane to that to which the liquid drug is supplied), for example, a hollow cylinder with a seal at one end. The cylinder is placed on top of the membrane and filled with cleaning liquid. The membrane is then vibrated so that the cleaning liquid is conveyed through the pores in the membrane in the reverse direction, thereby cleaning it. In one embodiment, the cleaning liquid supply means is a long tube which is inserted through the mouthpiece of the nebulizer device.

WO 2015/128375 discloses a cleaning unit for an aerosol generator based on this principle, in which the inhalation device is supplied with a cleaning unit. The inhalation device consists of an aerosol generator part (comprising the vibrating membrane and piezoelectric oscillator), a housing for the aerosol generator and a controller. When the membrane needs cleaning, the aerosol generator is removed from its housing and placed upside down into the cleaning unit. Cleaning liquid is supplied to the aerosol side of the membrane. The cleaning unit is then connected to the controller and the membrane is vibrated so that the cleaning liquid is conveyed through the pores in the membrane, thereby cleaning it.

However, these devices are specialised and can be expensive to produce. Thus there remains a need for an improved method for cleaning the membrane of a nebulizer.

BRIEF DESCRIPTION OF THE INVENTION

The present inventors have now recognized that this problem can be solved by using a disposable single-use container which contains a suitable cleaning liquid and which can be placed onto the aerosol generator of the nebulizer, for example in a push-fit or click-fit manner. The membrane is thereby immersed in the cleaning liquid, whilst being isolated from the surrounding environment, so that the cleaning fluid cannot become contaminated with dust etc. The method is easy to use, and therefore results in better patient compliance in cleaning the membrane. This in turn results in better and more predictable membrane performance, and hence more precise dosing of the drug during treatment. Moreover, the membrane can be kept in the container for the whole time between treatments, i.e. for storage in a hygienic environment ("maintenance") as well as for cleaning.

Accordingly, in a first aspect, the present invention provides a single-use, pre-packaged, sealed container for use with a nebulizer device having an aerosol generator comprising a membrane having pores, the container containing a cleaning liquid and being configured to fit onto the nebulizer device, so that the container is held in place on the nebulizer device and the membrane is immersed in the liquid.

Preferably the container is configured to provide a push-fit on the nebulizer device. More preferably the container has an opening that is sized and shaped to match the nebulizer device or part of the nebulizer device, in particular the aerosol generator. Most preferably the opening comprises a sealing member, preferably made from an elastomeric material.

Alternatively or additionally, the container may have formations which detachably hold the container in place on the nebulizer device.

Preferably the container is a blow-fill-seal container. Preferably the container is made from a recyclable material, in particular a recyclable plastic.

Preferably the volume of cleaning liquid in the container is from 0.1 to 5 mL, more preferably from 0.2 to 2 mL, most preferably from 0.5 to 1 mL.

Preferably the container has a tab which facilitates handling. More preferably, the tab is shaped to match a complementary indentation in the nebulizer device.

In one embodiment, the container forms a seal when held in place on the nebulizer device and has at least one collapsible and/or deformable and/or movable portion for reducing the volume in such a way as to cause the liquid to pass out of the container through the opening and into the pores of the membrane. The user deforms the container, for example by squeezing it with the thumb and index finger, thereby pressing the cleaning fluid into the pores and through the membrane. The seal is sufficient is such that little or none of the cleaning liquid leaks out when the container is deformed by the user. Preferably the container is in the form of bellows and has a flat base, or is in the form of a syringe.

In a second aspect, the present invention provides a method for cleaning the membrane of a nebulizer device having an aerosol generator comprising the membrane; the method comprising providing a pre-packaged, sealed container according to the first aspect of the invention; opening the container and placing it onto the nebulizer device; so that the membrane is immersed in the liquid and the container is held in place on the nebulizer device.

Preferably the nebulizer device has an ultrasonic aerosol generator which comprises a cylindrical transducer body having a vibrating membrane at its downstream end and the container has a circular opening whose diameter corresponds to the diameter of the downstream part of the transducer body. More preferably, the nebulizer device comprises a base unit, a mouthpiece and an aerosol head which are detachably connectible with each other, the base unit comprising one or more indentation(s), the mouthpiece comprising one or more positioning member(s) and a lateral opening, and the aerosol head comprising the aerosol generator; and wherein the container has a tab which is shaped to match the indentation(s); the method comprising: disconnecting the aerosol head from the base unit; removing the mouthpiece; placing the container in the base unit so that the tab is received into the indentation(s); and re-connecting the aerosol head with the base unit, so that the downstream part of the transducer body is inserted into the opening of the container.

Preferably the membrane is not vibrated while the container is in place on the nebulizer device.

Preferably the container remains in place on the nebulizer device for at least 5, 10 or 20 hours. Preferably the container remains in place for substantially the whole time between operations, in particular between treatments.

Preferably the nebulization device is a medical inhalation device.

In one embodiment, the method includes reducing the volume of the container in such a way as to cause the liquid to pass out of the container through the opening and into the pores of the membrane. Preferably the method includes the step of reducing the pressure in the transducer body, most preferably by using a suction pump. This has the effect of sucking cleaning liquid through the membrane.

In a third aspect, the present invention provides a strip comprising a plurality of containers according to the first aspect of the invention, wherein each container is detachable from the rest of the strip. Preferably the strip has a line of perforations between each container, thereby facilitating the detachment of each container from the strip.

In a fourth aspect, the present invention provides a pack comprising a multi-day supply of a drug and containers according to the first aspect of the invention. Preferably the pack contains at least 20 days' supply of drug and at least 20 containers, for example 30 or 60 days' supply and 30 or 60 containers.

DETAILED DESCRIPTION OF THE INVENTION

In the art, the term "nebulizer" is sometimes used to refer to the inhalation device as a whole, and sometimes used to refer to the part of the inhalation device which generates the aerosol; nonetheless, it is usually apparent from the context which of these is intended. In the present description, the terms "inhalation device" and "nebulizer device" refer to the device which the patient uses, and the term "aerosol generator" refers to the parts of the device which produce the aerosol; for example, in a vibrating mesh nebulizer device, the combination of the vibrator and the membrane, together with associated mounting elements, transducers etc. In some nebulizer devices, the aerosol generator is detachable from the remainder of the device.

The terms "mesh", "membrane", "perforated membrane" and "nozzle plate" are all used herein to refer to the component having small pores (through holes) which create the aerosol droplets.

The term "push-fit" means a fastening between two parts which is achieved by friction after the parts are pushed together, rather than by any other means of fastening such as interlocking formations. It is also sometimes called a friction-fit, interference fit or press fit.

The term "pre-packaged, sealed container" means a container which is filled, closed and sealed before it is provided to the user of the nebulizer device, so that the container has to be opened by the user in order to access the contents. Once the container has been opened, it is no longer sealed. Thus a re-closable container is only pre-packaged and sealed before it is first opened; it is not pre-packaged and sealed if it is subsequently re-closed.

The term "deformable" means that the container can be deformed by the user, for example by squeezing it between the thumb and index finger, or by pressing the container against a surface, so that the liquid pressure inside the container increases.

Embodiments of the invention will now be described, by way of example only, with reference to the accompanying drawings, in which.

Figure 1:
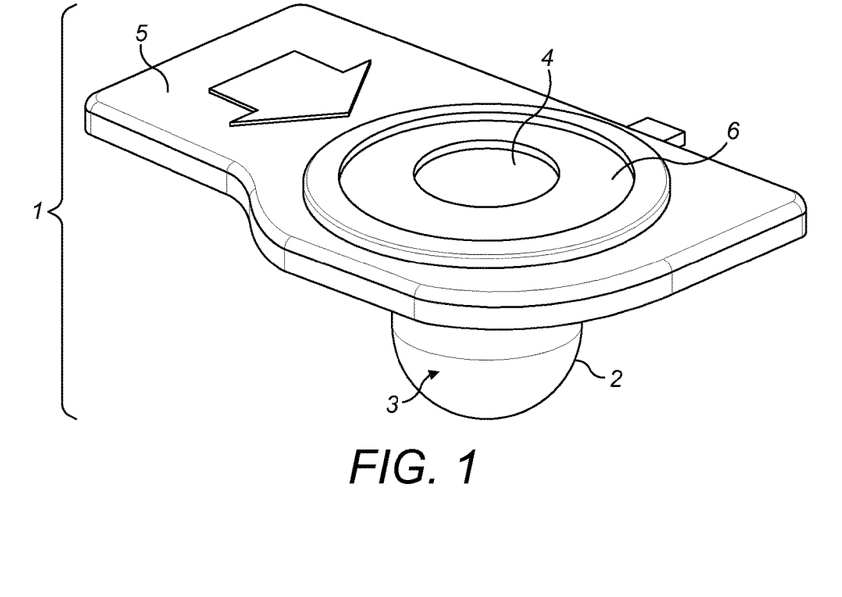
FIG. 1 shows a container according to the invention.

FIG. 1 shows a container 1 according to the invention. The container consists of a body 2 which contains the liquid 3 and an opening 4. The opening 4 is sealed by a cover (not shown) which is removed shortly before the container is placed onto the nebulizer device, or which is punctured as the container is placed onto the nebulizer device. The container has a tab 5 which facilitates handling of the container, e.g. when placing it onto the aerosol generator. The opening is defined by a sealing member 6. The sealing member shown in FIG. 1 is in the form of an annular ring; however, it may instead be a cross-slit valve or any other suitable seal which forms a push-fit on the aerosol generator. Alternatively, the container may not have a sealing member, in which case the opening is simply the correct size and shape to form a push-fit on the aerosol generator. The diameter of the opening of the container (which is defined by the sealing member 6 if present) is preferably from about 6 mm to about 8 mm, such as about 7 mm. Suitably, the depth of the container is similar, i.e. from about 6 mm to about 8 mm, such as about 7 mm.

In addition to, or instead of the push-fit, the container and/or the nebulizer device may have formations which detachably hold the container in place on the nebulizer device, in particular on the aerosol generator. For example the formations may be a cam and groove or interlocking members, which form a click-fit.

Figure 2:
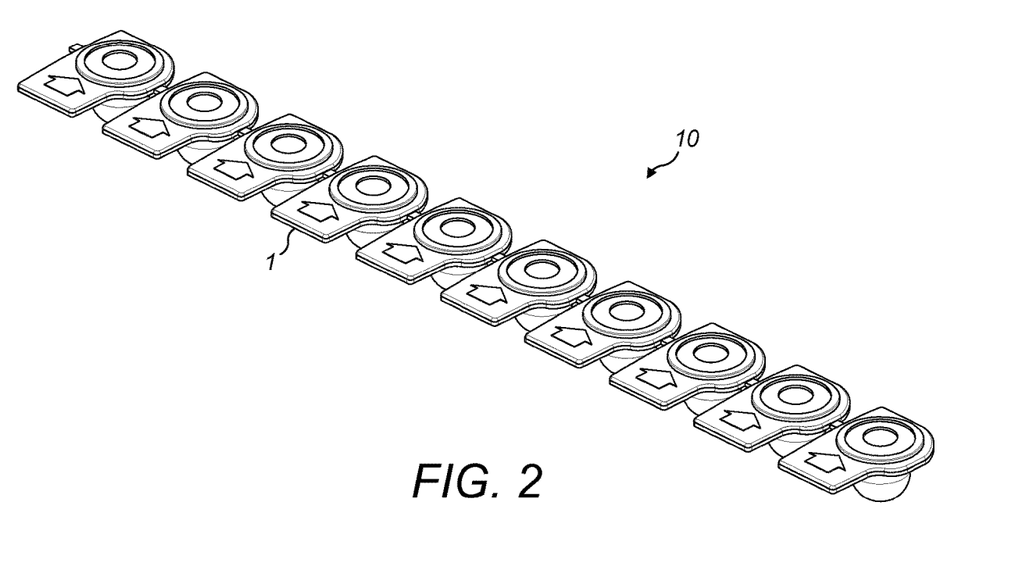
FIG. 2 shows a strip of ten containers.

The containers may be provided in the form of a strip 10 of several (e.g. 7 or 10) containers 1, shown in FIG. 2. Each container is detachable from the rest of the strip, for example by virtue of a line of perforations between each container, so that individual containers can be detached as needed. A number of containers may be provided together with the drug, for example 30 days' supply of drug together with 30 cleaning containers or 60 days' supply of drug and 60 containers.

Figure 3:
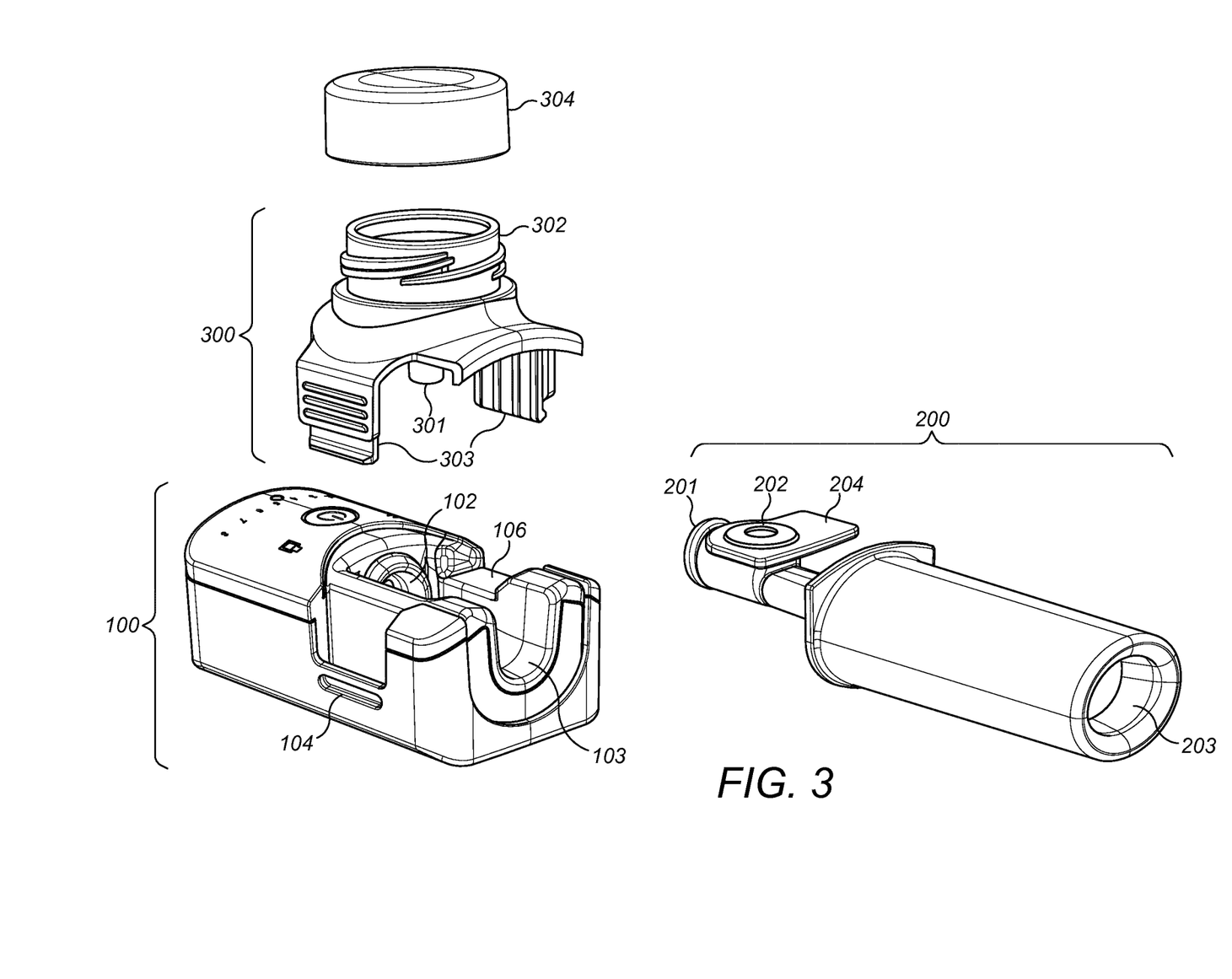
FIG. 3 shows a nebulizer device.

The container is suitable for use with the nebulizer device shown in FIG. 3, which is described in detail in EP2724741. The device comprises three parts: a base unit, a mouthpiece, and an aerosol head. The base unit 100 has one or more air inlet opening(s), an air outlet opening 102, a groove 103 for receiving the mouthpiece 200, and one or more key lock members 104. The mouthpiece 200 has an air inlet opening 201 which is attachable to the air outlet opening 102 of the base unit 100, a lateral opening 202 for receiving an aerosol generator 301, and an aerosol outlet opening 203. The mouthpiece 200 is insertable into the groove 103 of the base unit 100. The aerosol head 300 has an aerosol generator 301, a reservoir 302 for the liquid drug formulation to be nebulized, which is in fluid contact with the upper end of the aerosol generator 301, and one or more key lock members 303 complementary to the key lock members 104 of the base unit 100. A lid 304 closes the upper end of the reservoir 302 and prevents contamination or spillage of the liquid during use.

The base unit 100, the mouthpiece 200 and the aerosol head 300 are detachably connectible with one another. The device is assembled by inserting the mouthpiece 200 into the groove 103 in the base unit 100, then placing the aerosol head 300 over the mouthpiece 200 and engaging the key lock member(s) 303 of the aerosol head 300 with the complementary member(s) 104 of the base unit 100 by gentle pressure on both the aerosol head and the base unit. The aerosol generator 301 is positioned in the aerosol head 300 in such a way that when engaging the key lock member(s), the aerosol generator 301 is inserted into the lateral opening 202 of the mouthpiece 200. This creates airtight connections between the aerosol generator 301 and the lateral opening 202 in the mouthpiece as well as between the air outlet opening 102 of the base unit 100 and the air inlet opening 201 of the mouthpiece 200. The base unit 100, the mouthpiece 200 and the aerosol head 300 can be separated by reversing these steps.

The base unit 100 may have one or more indentation(s) 106 whose position may be at or near the groove 103, and the mouthpiece 200 may have one or more positioning member(s) 204. The indentation(s) of the base unit are complementary to (i.e. shaped to receive) the positioning member(s) 204 of the mouthpiece 200. In this context, an indentation is a depression (e.g. a recess, pit, cavity, void, notch or the like) whose "negative" shape is complementary to the "positive" shape of a positioning member (which may be a flange, projection, nose, bulge or the like). Together, such indentations and positioning members act to position the mouthpiece correctly in the base unit. The indentation(s) 106 and the positioning member(s) 204 may be asymmetrical, so as to ensure that the mouthpiece 200 can only be inserted into the indentation 106 of the base unit 100 in one particular manner. This ensures that the device is assembled in such a way that the position and orientation of the mouthpiece 200 and base unit 100 relative to each other are correct.

Figure 4:
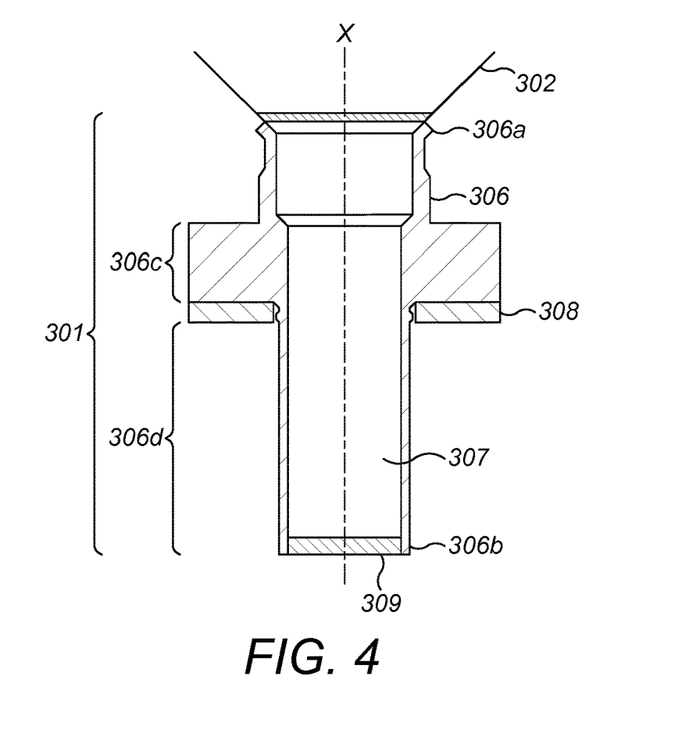
FIG. 4 shows the aerosol generator for the nebulizer device of FIG. 3.
Figure 5:
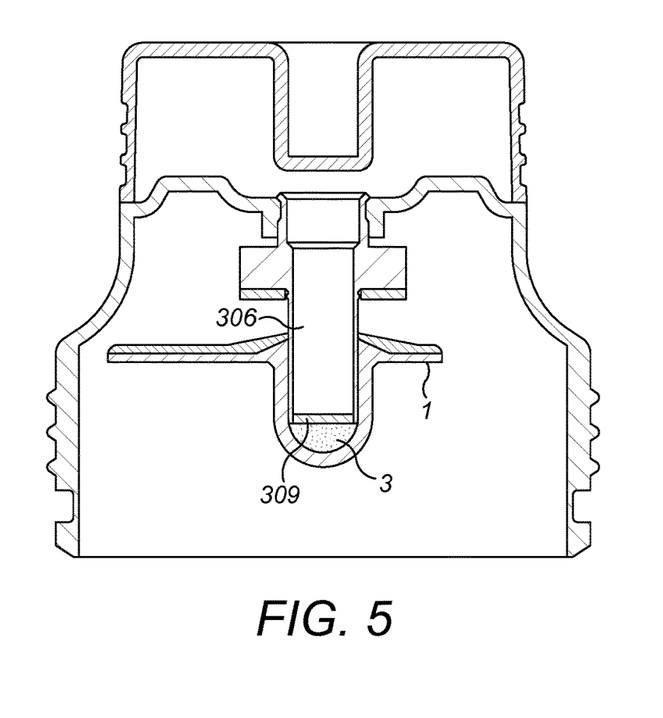
FIG. 5 shows a container in place on the aerosol generator of FIG. 4.
Figure 6:
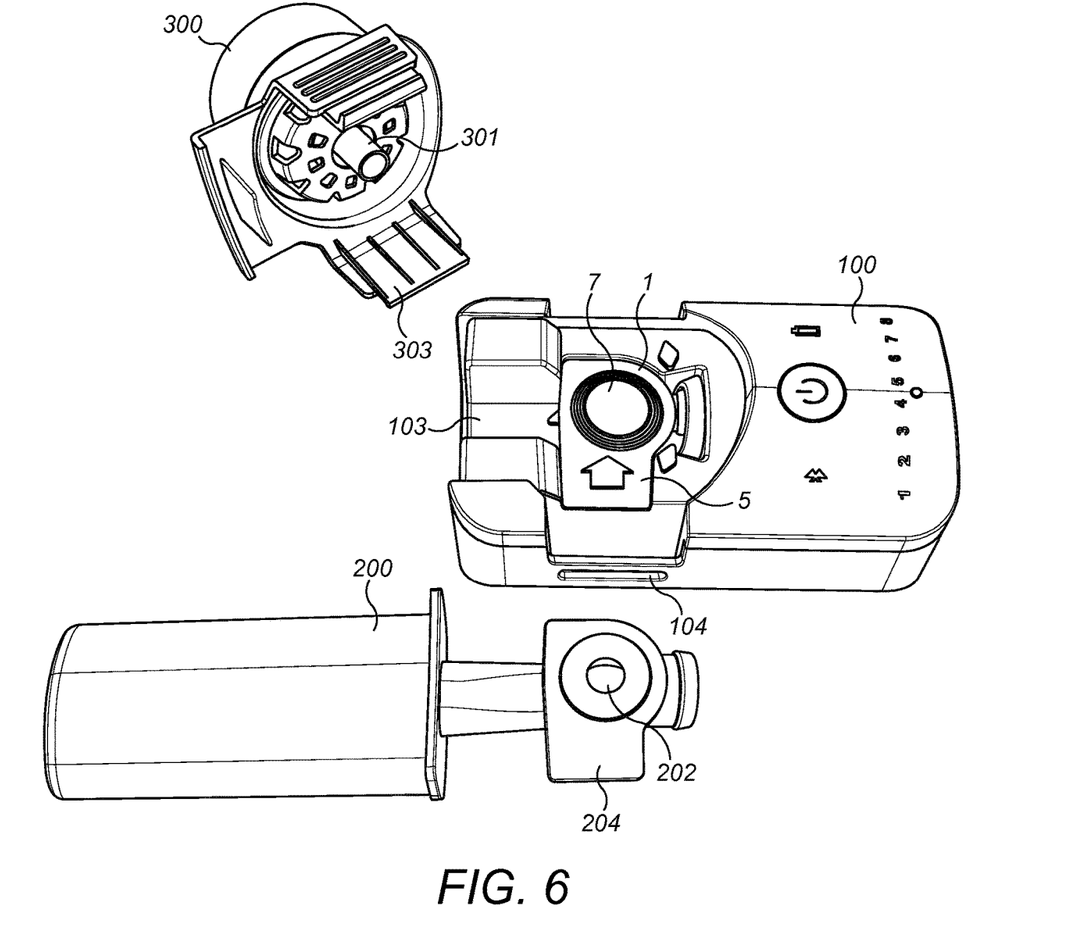
FIG. 6 shows a container in place in the base unit of the nebulizer device of FIG. 3.
Figure 7:
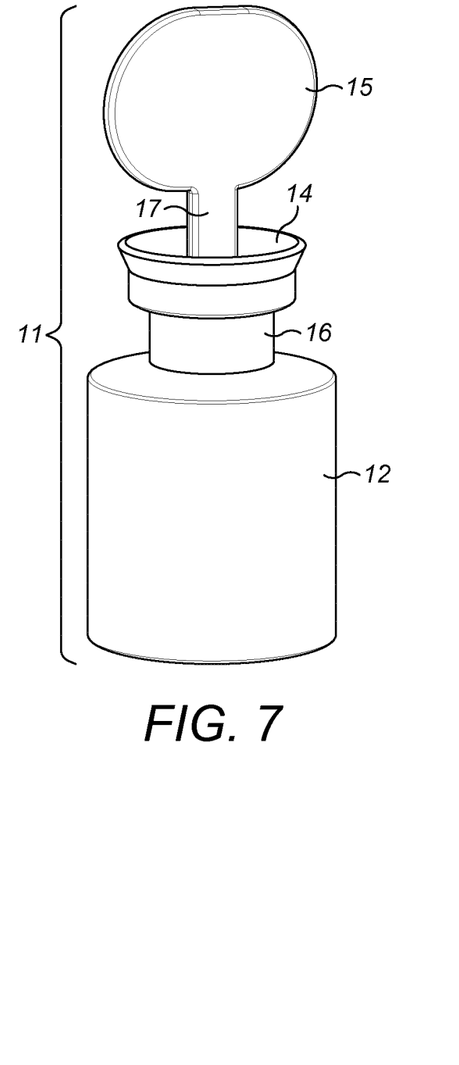
FIG. 7 shows a second embodiment of container according to the invention.

The aerosol generator is preferably an ultrasonic liquid atomiser comprising a piezoelectric member 308 and a transducer body 306 as shown in FIG. 4 and described in WO 2008/058941. The transducer body 306 is, for example made of stainless steel, titanium or aluminium, and encloses a cavity 307 which contains the liquid to be nebulized. The cavity 307 is in fluid contact with the reservoir 302 so as to receive liquid to be nebulized from it. The reservoir 302 is optionally shaped as a funnel, or truncated cone, or a tapered cylinder, with the narrower end transitioning into the upstream end 306a of the aerosol generator 301, such as to ensure easy, gravity-driven liquid flow from the reservoir 302 into the aerosol generator 301.

The piezoelectric member 308 is preferably an annular single or multilayer ceramic, which vibrates the transducer body 306 in a longitudinal mode, at a frequency preferably in the 50 to 200 kHz range. As a result, micronic longitudinal displacements, or deformations, occur in a direction parallel to the symmetry axis of the transducer body 306. The transducer body 306 has a region close to the piezoelectric member 308 with a relatively large wall thickness, which serves as a stress concentration zone 306c, and a region downstream thereof 306d with a relatively low wall thickness which serves as a deformation amplification zone. In this configuration, the vibrations or deformations of the transducer body 306 caused by the piezoelectric member 308 are amplified. Preferably, the piezoelectric member 308 is located at the level of, or adjacent to, the stress concentration zone 306c. The internal diameter of the transducer body 306 at the deformation amplification zone 306d may be the same as at the stress concentration zone 306c, so that the differences in wall thickness correspond to different external diameters. Alternatively, the external diameter of the transducer body 306 may be constant, while the inner diameters differ at the position of the two zones.

Figure 9:
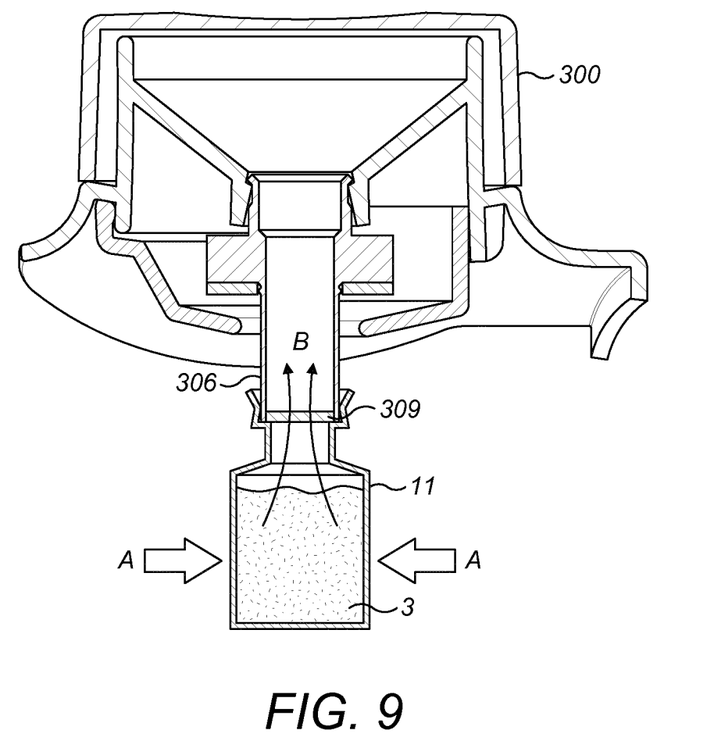
FIG. 9 shows the container of FIG. 7 in place on the aerosol generator of FIG. 4.

A membrane 309 is positioned at the downstream end 306b of the transducer body 306. The holes may be formed by electroforming or by laser drilling, with openings normally being in the range from about 1 μm to about 10 μm. Without vibration of the membrane, the balance of pressures, the shape of the holes and the nature of the material used for the membrane are such that the liquid does not seep out through the membrane. However, vibration of the membrane leads to the formation and emission of aerosol droplets through the holes. The membrane may be made of plastic, silicon, ceramic or more preferably metal, and may be affixed to the downstream end 306b of the aerosol generator 301 by various means, such as gluing, brazing, crimping or laser welding. Optionally, the membrane at least partially forms a dome in its central region, which causes the jet of nascent aerosol droplets to diverge and hence reduces the risk of droplet coalescence.

Once a treatment operation has been completed, the aerosol head key lock members 303 are disengaged from the complementary member(s) 104 of the base unit 100, so that the aerosol generator 301 can be removed from the lateral opening 202 of the mouthpiece 200. Then a container 1 is opened, for example by removing or puncturing the cover, and placed onto the transducer body 306 of the aerosol generator, as shown in FIG. 5. The container 1 has a circular opening whose diameter corresponds to the diameter of the cylindrical lower (downstream) part 306*d* of the transducer body, thereby creating a push-fit connection when the container is placed onto the transducer body 306. If the container is made from a flexible material, a sealing member is not necessary, and the diameter of the opening of the container matches the diameter of the downstream part 306*d* of the transducer body. Alternatively, if the container has a sealing member 6, the diameter of the opening is defined by the internal diameter of the sealing member, which accordingly corresponds to the diameter of the downstream part 306*d* of the transducer body. For example, the downstream part 306*d* of the transducer body may have a diameter of 7 mm, and correspondingly, the opening of the container also has a diameter of 7 mm.

Thus the membrane 309 is immersed in the liquid 3 in the container 1 while the membrane 309 is in situ on the aerosol generator. Consequently, it is not necessary to remove the membrane 309 from the aerosol generator 301 in order to clean it.

In a preferred embodiment illustrated in FIG. 6, the tab 5 of the container 1 is shaped to match the positioning member(s) 204 of the mouthpiece 200 so that the tab 5 is received in the indentation 106 and acts as a positioning member for the container 1 in the same manner as the positioning member(s) 204 of the mouthpiece 200. This allows the container 1 to be located in the base unit 100 in place of the mouthpiece 200 during the cleaning step. The cover 7 is removed either before or after placing the container in the base unit. The aerosol head 300 is then placed onto the base unit by engaging the key lock members 104, 303, in the same manner as described above for a treatment operation. Instead of removing the cover 7, it could alternatively be pierced or punctured as the aerosol generator is inserted into the opening 4. The opening 4 of the container 1 matches the size and shape of the lateral opening 202 of the mouthpiece 200. Thus the downstream part 306*d* of the transducer body is inserted into opening 4 of the container 1 thereby forming a push-fit connection when the aerosol head 300 is placed onto the base unit 100.

The components are assembled in the same manner for both a treatment operation and a cleaning step, the only difference being the replacement of the mouthpiece with the container. This has the advantage that the aerosol generator 300 and container 1 are situated inside the base unit 100 during the cleaning step. In this way, the aerosol generator and membrane are protected from accidental damage during the cleaning step, without requiring a separate unit or holder in which to place them (as in WO 2015/128375 for example). Furthermore, it is very straightforward and intuitive for the user, whilst avoiding any possibility of the container being inserted in the wrong position or orientation. It also allows the membrane to be vibrated during the cleaning step, in the same manner as during a treatment step (although, as explained below, this is not necessary).

FIG. 7 shows a second embodiment of a container 11 according to the invention. The container consists of a cylindrical body 12 which contains the cleaning liquid and a neck 16, at the upper end of which is an opening 14. The opening 14 is sealed by a lid 17 which is removed shortly before the container is placed onto the nebulizer device. The lid 17 has a grip 15 which is pulled in order to remove the lid from the container, before placing it onto the nebulizer. The opening may have a sealing member, for example an annular ring or a cross-slit valve or any other suitable seal. Alternatively, the container may not have a sealing member, in which case the opening 14 and neck 16 are the correct size and shape to form a push-fit on the aerosol generator of the nebulizer device.

FIG. 8 shows a third embodiment of a container 11 according to the invention. The container is similar to the second embodiment, except that the body 12 is in the form of bellows.

The neck 16 may have a flared portion at its upper end to facilitate placing the container onto the transducer body 306, which leads onto a first cylindrical portion which forms the push-fit. Beneath this the neck may have a second cylindrical portion which is narrower than the transducer body. The step formed at the join between the two cylindrical portions thus limits the extent to which the transducer body can enter the neck. Nonetheless, the narrower portion is at least as wide as the membrane so that none of the membrane is covered by the step, in order that the cleaning liquid can reach the whole of the membrane.

FIG. 9 shows the container of FIG. 7 in use. The user holds the aerosol 300 head with one hand, and then gently squeezes the container 11 by pressing it between the index finger and the thumb of the other hand (arrows A). The deformation of the container body generates a fluid pressure so that some or all of the cleaning liquid 3 is pressed through the pores of the membrane 309 (arrows B) and cleans them. The push-fit between the first portion of the neck and the transducer body 306 should form a sufficiently tight seal so that little or none of the cleaning liquid leaks out when the container is squeezed.

Figure 8:
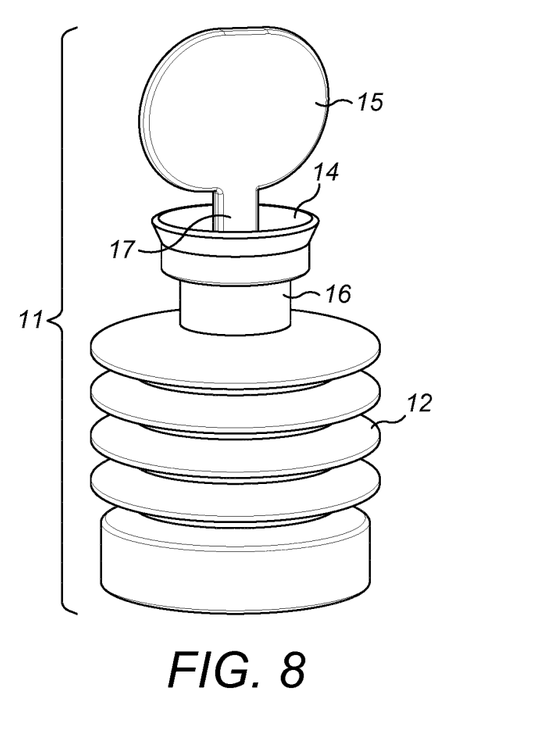
FIG. 8 shows a third embodiment of container according to the invention.
Figure 10:
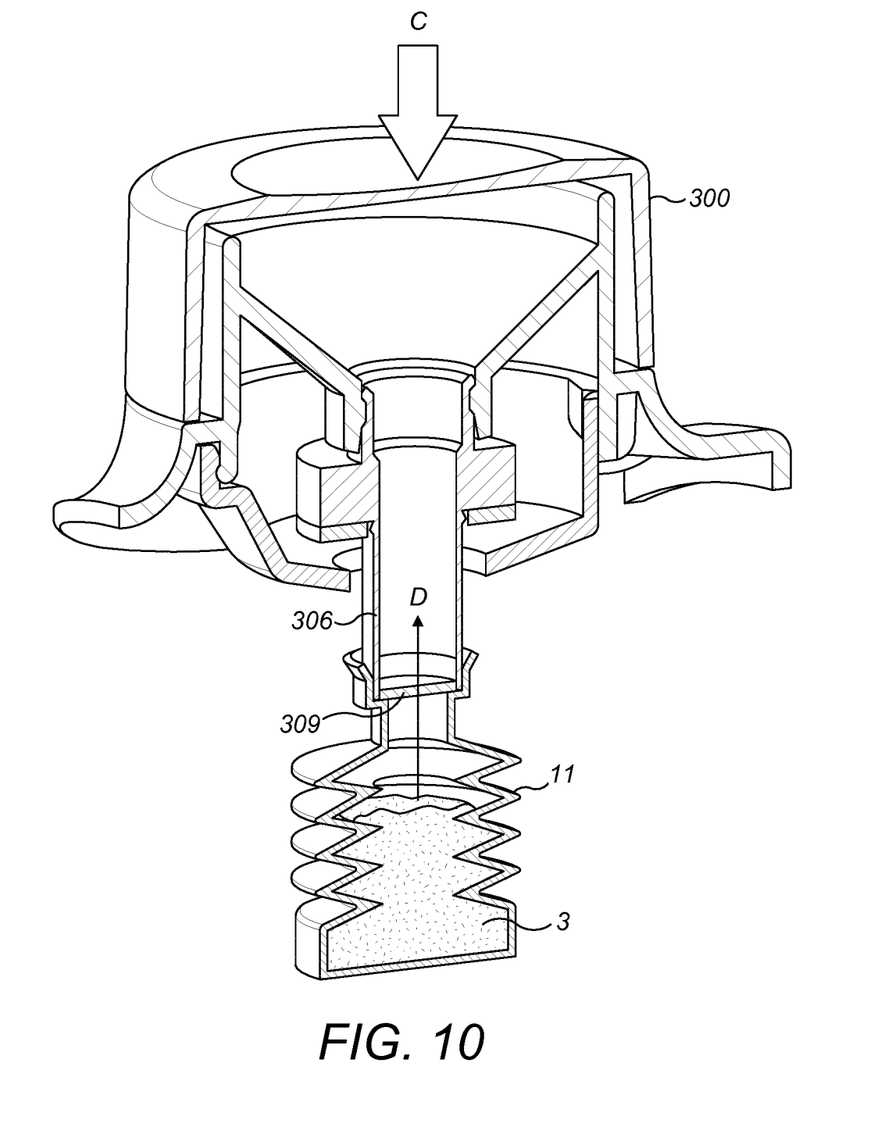
FIG. 10 shows the container of FIG. 8 in place on the aerosol generator of FIG. 4.

FIG. 10 shows the container of FIG. 8 in use. The body of the container 11 is in the form of bellows. The user holds the aerosol head 300 so that the base of the container rests on a flat surface. Then the nebuliser head is pressed downwards (arrow C), so that the bellows compress and the fluid pressure within the container rises. Some or all of cleaning liquid 3 is pressed through the pores of the membrane 309 (arrow D) and cleans them. This embodiment has the advantage of allowing the user to exert greater pressure on the fluid very easily.

Figure 11:
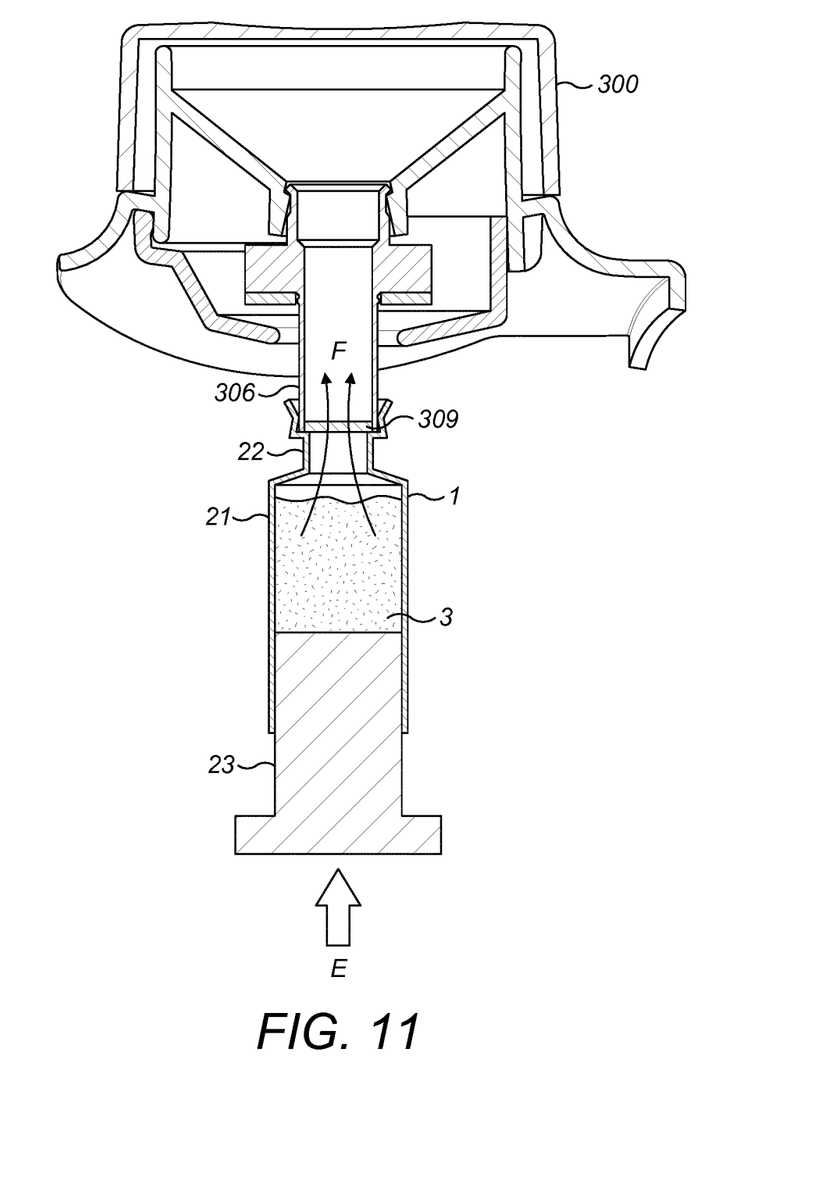
FIG. 11 shows a fourth embodiment of container in place on the aerosol generator of FIG. 4.

FIG. 11 shows a fourth embodiment, wherein the container is in the form of a syringe having a barrel 21 with a nozzle 22 at one end and a movable plunger 23 at the other end. The plunger fits tightly within the barrel. The nozzle forms the opening which fits onto the transducer body. Cleaning liquid 3 is filled into the barrel, and the plunger is moved into the barrel (arrow E), thereby forcing cleaning liquid into and through the pores of the membrane 309 (arrow F).

As with the first embodiment, in the second, third and fourth embodiments, the diameter of the opening of the container (which is defined by the sealing member if present) may form a push-fit and is preferably from about 6 mm to about 8 mm, such as about 7 mm. In addition to, or instead of the push-fit, the container and/or the nebulizer device may have formations which detachably hold the container in place on the nebulizer device, in particular on the aerosol generator. For example the formations may be a cam and groove or interlocking members, which form a click-fit.

Figure 12:
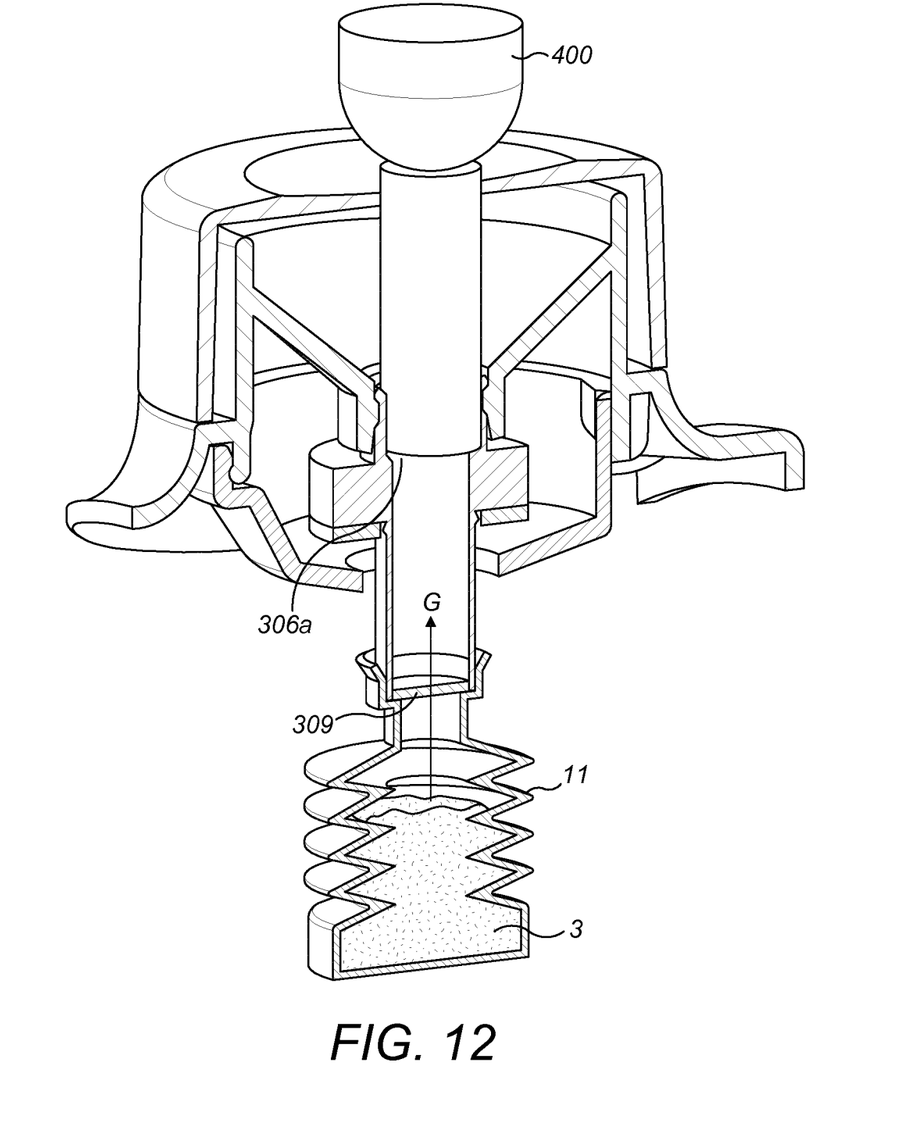
FIG. 12 shows a variation of FIG. 10, in which a suction pump is additionally used.

With the second, third or fourth embodiment, it is also possible to connect a suction pump 400 to the reservoir or to the upstream end of the transducer body 306a, as shown in FIG. 12. This allows the pressure to be reduced on the liquid (drug) side of the membrane, thereby sucking cleaning fluid 3 through the membrane 309 (arrow G) and removing residues from the pores. The pump may be a bellows pump or any other means to generate suction.

The cleaning liquid may contain detergents, anti-bacterial substances and/or specific chemicals for maintaining the performance of the membrane. For example, the cleaning liquid may be isopropanol, acetone, saline solution, hydrogen peroxide, ethanol or a mix (e.g. 50/50) of ethanol and water. Alternatively the cleaning liquid may simply be water, in particular distilled water. The cleaning liquid may be selected according to the drug being used. For example, if the drug is budesonide, the cleaning liquid is preferably a mixture of ethanol and water. Alternatively, if the liquid to be nebulized contains protein, the cleaning liquid is preferably hydrogen peroxide.

Typically, the container contains 0.1 to 5 mL of cleaning liquid, preferably from 0.2 to 2 mL, most preferably from 0.5 to 1 mL. The container is typically small (<5 cm in size), and is therefore easy to store and transport along with the nebulizer, for example when the patient is away from home on holiday or during a business trip.

The container is preferably not completely full of the cleaning liquid before it is placed onto the nebulizer, so that when the membrane is immersed in the liquid, the liquid does not overflow out of the container. Preferably the cleaning liquid occupies between about 50% and 90% of the internal volume of the container before the membrane is immersed, more preferably between about 60 and 85%.

The container is intended for single use only, and consequently it is preferably made from a recyclable material, in particular a recyclable plastic such as polypropylene. Preferably, the container is a blow-fill-seal container so that the liquid is stored aseptically.

Two (or more) different containers may be used, for example one containing a first liquid containing a cleaning agent, such as detergent or hydrogen peroxide; and the other containing a second liquid for maintenance/storage (e.g. distilled water). In this case, the cleaning container is typically placed onto the nebulizer device for a pre-determined period of time, such as 10 minutes; then it is removed and the maintenance/storage container is placed onto the nebulizer device and remains in place until the next treatment operation. Using two different containers has the advantage that any residual cleaning agent from the first liquid is removed into the second liquid. Consequently, good cleaning of the membrane is achieved without the cleaning agent being aerosolized, and hence potentially transmitted to the patient. The containers for the first and second liquids are preferably easily distinguished, for example they may be different colours.

Similarly, for some active materials, it may be desirable to sequentially use three (or more) containers with different cleaning liquids. For example, the first container may contain hydrogen peroxide; and the second container may contain an ethanol/water mixture. These may be followed by a third container with distilled water.

The container may be placed onto the nebulizer device for the purposes of cleaning only, for example for a relatively short period of time. Preferably however, the container remains in place for substantially all of the time period between treatment operations, thereby not only cleaning the membrane, but also maintaining it in a hygienic environment. Thus, when two or more containers are used, then one of the containers, in particular the final one, remains in place for substantially all of the time period after the initial cleaning step and before the next treatment operation. For example a container may be in place for at least 5 hours, preferably at least 10 hours, more preferably at least 20 hours. The container is removed before the next treatment operation, after which a new container is placed onto the nebulizer device for the subsequent cleaning step.

The method may comprise the further step of vibrating the membrane while it is immersed in the cleaning liquid in a cleaning cycle. The cleaning cycle may be started manually, for example by pushing a button on the nebulizer. Alternatively, the cleaning cycle is initiated automatically, for example because when the container is placed on to the nebulizer device, the nebulizer recognises the container e.g. by means of electrical contacts. However, due to the extended time for which the membrane can be in contact with the cleaning liquid, it is not necessary to vibrate the membrane whilst it is immersed in the cleaning liquid. Thus, in a preferred method, the membrane is not vibrated whilst it is immersed in the cleaning liquid.

Although not limited to these applications, the main focus of interest in the present application lies in aerosol generators for medical inhalation therapies and nebulization devices.

The invention claimed is:

1. A single-use pre-packaged, sealed container for use with a nebulizer device having an aerosol generator comprising a membrane having pores, the container having a depth of from 6 to 8 mm and containing from 0.1 to 5 mL of a cleaning liquid and comprising an opening that is circular with a diameter of from 6 to 8 mm and a cover or lid that seals the opening, the opening being configured to provide a push-fit onto the aerosol generator once the opening is unsealed, so that the container is held in place on the nebulizer device and the membrane is immersed in the cleaning liquid.

2. The container of claim 1, where in the opening comprises a sealing member.

3. The container of claim 2, wherein the sealing member comprises an elastomeric material.

4. The container of claim 1, further comprising formations configured to detachably hold the container in place on the nebulizer device.

5. The container of claim 1, wherein a volume of cleaning liquid in the container is from 0.5 to 1 mL.

6. The container of claim 1, further comprising a tab, wherein the nebulizer device further comprises an indentation, and wherein the tab is shaped to match the indentation of the nebulizer device.

7. A strip comprising a plurality of containers of claim 1, wherein each container is detachable from the rest of the containers in the strip.

8. A pack comprising a multi-day supply of a drug and a plurality of containers of claim 1.

9. The container of claim 1, wherein the opening is sized and shaped to receive the aerosol generator so that the membrane is immersed in the cleaning liquid when the container is fit onto the nebulizer device.

10. The container of claim 1, wherein a volume of cleaning liquid in the container is from 0.2 to 2 mL.

11. The container of claim 1, wherein the diameter of the opening is about 7 mm.

\* \* \* \* \*